US012214192B2

(12) United States Patent
Dassos et al.

(10) Patent No.: US 12,214,192 B2
(45) Date of Patent: Feb. 4, 2025

(54) BAND WITH BUILT-IN STIMULATOR

(71) Applicant: ResMed Pty Ltd, Bella Vista (AU)

(72) Inventors: Peter James Dassos, Sydney (AU); Benjamin Peter Johnston, Sydney (AU); Nathan Zersee Liu, Sydney (AU); Sakeena De Souza, Sydney (AU); Mark Neil Phillips, Sydney (AU); Genevieve Claire Madafiglio, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 450 days.

(21) Appl. No.: 17/623,124

(22) PCT Filed: Jun. 26, 2020

(86) PCT No.: PCT/IB2020/056092
§ 371 (c)(1),
(2) Date: Dec. 27, 2021

(87) PCT Pub. No.: WO2020/261226
PCT Pub. Date: Dec. 30, 2020

(65) Prior Publication Data
US 2022/0401728 A1    Dec. 22, 2022

Related U.S. Application Data

(60) Provisional application No. 62/868,336, filed on Jun. 28, 2019.

(51) Int. Cl.
*A61N 1/36* (2006.01)
*A61B 5/00* (2006.01)
(Continued)

(52) U.S. Cl.
CPC ...... *A61N 1/36031* (2017.08); *A61B 5/02416* (2013.01); *A61B 5/0826* (2013.01);
(Continued)

(58) Field of Classification Search
CPC ............ A61N 1/36031; A61B 5/02416; A61B 5/0826
(Continued)

(56) References Cited

U.S. PATENT DOCUMENTS 5,190,036 A    3/1993   Linder
5,265,624 A    11/1993  Bowman
(Continued)

FOREIGN PATENT DOCUMENTS

| JP | 2007502670 A | 2/2007 |
| JP | 2009515670 A | 4/2009 |
| WO | 1998/041279 A1 | 9/1998 |

OTHER PUBLICATIONS

International Search Report in International Patent Application No. PCT/IB2020/056092 mailed Sep. 4, 2020 (17 pp.).
(Continued)

*Primary Examiner* — Nadia A Mahmood
(74) *Attorney, Agent, or Firm* — Nixon Peabody LLP (57) ABSTRACT

A system includes a collar that is worn around a neck of the user. A stimulator is coupled to the collar such that the stimulator is positioned adjacent to an airway of the user. The sensor is coupled to the collar and configured to generate data associated with the airway of the user. The memory is coupled to the collar and storing machine-readable instructions. The control system is coupled to the collar and includes one or more processors configured to execute the machine-readable instructions to determine, based at least on an analysis of the generated data, that the user is currently experiencing an apnea event. In response to the determination, the control system causes the stimulator to provide electrical stimulation, at a first intensity level, to one or more muscles of the user that are adjacent to the airway to aid in stopping the apnea event.

27 Claims, 6 Drawing Sheets

(51) Int. Cl.
    *A61B 5/024*     (2006.01)
    *A61B 5/08*      (2006.01)
    *A61N 1/04*      (2006.01)
(52) U.S. Cl.
    CPC .......... *A61B 5/4818* (2013.01); *A61B 5/6822* (2013.01); *A61B 5/6823* (2013.01); *A61B 5/6831* (2013.01); *A61N 1/0452* (2013.01); *A61N 1/3601* (2013.01)
(58) Field of Classification Search
    USPC .......................................................... 607/42
    See application file for complete search history.

(56) References Cited

U.S. PATENT DOCUMENTS

| | | |
|---|---|---|
| 6,935,335 B1 | 8/2005 | Lehrman et al. |
| 2005/0107838 A1* | 5/2005 | Lovett .................. A61B 5/4818 |
| | | 607/42 |
| 2006/0145878 A1 | 7/2006 | Lehrman et al. |
| 2008/0009755 A1 | 1/2008 | Patangay et al. |
| 2013/0197321 A1 | 8/2013 | Wilson |
| 2014/0051938 A1 | 2/2014 | Goldstein et al. |
| 2018/0078761 A1 | 3/2018 | Bolea et al. |
| 2018/0326209 A1 | 11/2018 | Gelfand et al. |

OTHER PUBLICATIONS

Written Opinion in International Patent Application No. PCT/IB2020/056092 mailed Sep. 4, 2020 (13 pp.).

* cited by examiner

BAND WITH BUILT-IN STIMULATOR

CROSS-REFERENCE TO RELATED APPLICATIONS

This application is a U.S. National Stage of International Application No. PCT/IB2020/056092, filed Jun. 26, 2020, which claims the benefit of, and priority to, U.S. Provisional Patent Application No. 62/855,487, filed May 31, 2019, each of which is hereby incorporated by reference herein in its entirety.

TECHNICAL FIELD

The present disclosure relates to treatment of respiratory-related disorders and more specifically to systems and methods with bands having stimulators for addressing one or more types of apnea events.

BACKGROUND

Various systems exist for aiding users experiencing sleep apnea and related respiratory disorders. Some such systems rely on the user to wear a mask that aids in suppling pressurized air to the airway of the user. Some users find such systems to be uncomfortable, difficult to use, expensive, aesthetically unappealing, etc.

Thus, a need exists for alternative systems and methods for addressing sleep apnea and related respiratory disorders. The present disclosure is directed to solving these problems and addressing other needs.

SUMMARY

According to some implementations of the present disclosure, a method for aiding a user includes receiving, from one or more sensors, data associated with an airway of the user. The method further includes analyzing the data to determine (i) if the user is experiencing an apnea event, (ii) if the user is about to experience an apnea event, (iii) if the user is no longer experiencing an apnea event, (iv) or any combination thereof. The method further includes causing a stimulator to provide electrical stimulation to aid in stopping or preventing the apnea event in response to a determination that (i) the user is experiencing an apnea event or (ii) the user is about to experience an apnea event.

According to some implementations of the present disclosure, a system for aiding a user includes a collar, a stimulator, a sensor, a memory, and a control system. The collar is configured to be worn around a neck of the user. The stimulator is coupled to the collar such that, when the collar is worn around the neck of the user, the stimulator is positioned to provide electrical stimulation to (i) one or more muscles of the user that are adjacent to an airway of the user, (ii) one or more nerves associated with the one or more muscles, or (iii) both (i) and (ii). The sensor is coupled to the collar such that, when the collar is worn around the neck of the user, the sensor is configured to generate data associated with the airway of the user. The memory stores machine-readable instructions. The control system includes one or more processors configured to execute the machine-readable instructions to analyze the generated data to determine (i) if the user is experiencing an apnea event, (ii) if the user is about to experience an apnea event, (iii) if the user is no longer experiencing an apnea event, (iv) or any combination thereof. In response to a determination that (i) the user is experiencing an apnea event or (ii) the user is about to experience an apnea event, the control system causes the stimulator to provide the electrical stimulation to aid in stopping or preventing the apnea event.

According to some implementations of the present disclosure, a method for aiding a user includes receiving, from one or more sensors, data associated with an airway of the user. The method further includes determining, based at least in part on the data, that the user is currently experiencing an apnea event. The method further includes causing, in response to determining that the user is currently experiencing an apnea event, a stimulator to provide electrical stimulation, at a first intensity level, to one or more muscles of the user that are adjacent to the airway to aid in stopping the apnea event.

According to some implementations of the present disclosure, a system for aiding a user includes a collar, a stimulator, a sensor, a memory, and a control system. The collar is configured to be worn around a neck of the user. The stimulator is coupled to the collar such that, when the collar is worn around the neck of the user, the stimulator is positioned adjacent to an airway of the user. The sensor is coupled to the collar and configured to generate data associated with the airway of the user. The memory is coupled to the collar and storing machine-readable instructions. The control system is coupled to the collar and includes one or more processors configured to execute the machine-readable instructions to determine, based at least on an analysis of the generated data, that the user is currently experiencing an apnea event. In response to the determination that the user is currently experiencing an apnea event, the control system causes the stimulator to provide electrical stimulation, at a first intensity level, to one or more muscles of the user that are adjacent to the airway to aid in stopping the apnea event.

According to some implementations of the present disclosure, a method for aiding a user in breathing during sleep includes receiving, from a first sensor, first data. The method further includes receiving, from a second sensor, second data. The method further includes analyzing the first data to determine if the user is currently experiencing a first type of apnea event. The method further includes analyzing the second data to determine if the user is currently experiencing a second type of apnea event that is different than the first type of apnea event. The method further includes in response to determining that the user is currently experiencing the first type of apnea event based on the analyzing the first data, causing a first stimulator to provide electrical stimulation to one or more muscles of the user that are adjacent to an airway of the user to aid in stopping the first type of apnea event. The method further includes in response to determining that the user is currently experiencing the second type of apnea event based on the analyzing the second data, causing a second stimulator to provide the electrical stimulation to a diaphragm of the user to aid in stopping the second type of apnea event.

According to some implementations of the present disclosure, a system for aiding a user in breathing during sleep includes a first band, a first stimulator, a second band, a second stimulator, a first sensor, a second sensor, a memory, and a control system. The first band is configured to be worn around a neck of the user. The first stimulator is coupled to the first band such that, when the first band is worn around the neck of the user, the first stimulator is positioned to provide electrical stimulation to one or more muscles of the user that are adjacent to an airway of the user. The second band is configured to be worn around a chest or abdomen of the user. The second stimulator is coupled to the second band such that, when the second band is worn around the chest or abdomen of the user, the second stimulator is positioned to provide electrical stimulation to a diaphragm of the user. The first sensor is coupled to the first band and configured to generate first data. The second sensor is coupled to second band and configured to generate second data. The memory stores machine-readable instructions. The control system includes one or more processors configured to execute the machine-readable instructions to: (i) analyze the generated first data to determine if the user is currently experiencing a first type of apnea event and (ii) analyze the generated second data to determine if the user is currently experiencing a second type of apnea event that is different than the first type of apnea event. In response to a determination that the user is currently experiencing the first type of apnea event, the control system causes the first stimulator to provide the electrical stimulation to the one or more muscles of the user that are adjacent to the airway of the user to aid in stopping the first type of apnea event. In response to a determination that the user is currently experiencing the second type of apnea event, the control system causes the second stimulator to provide the electrical stimulation to the diaphragm of the user to aid in stopping the second type of apnea event.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

Figure 1A:
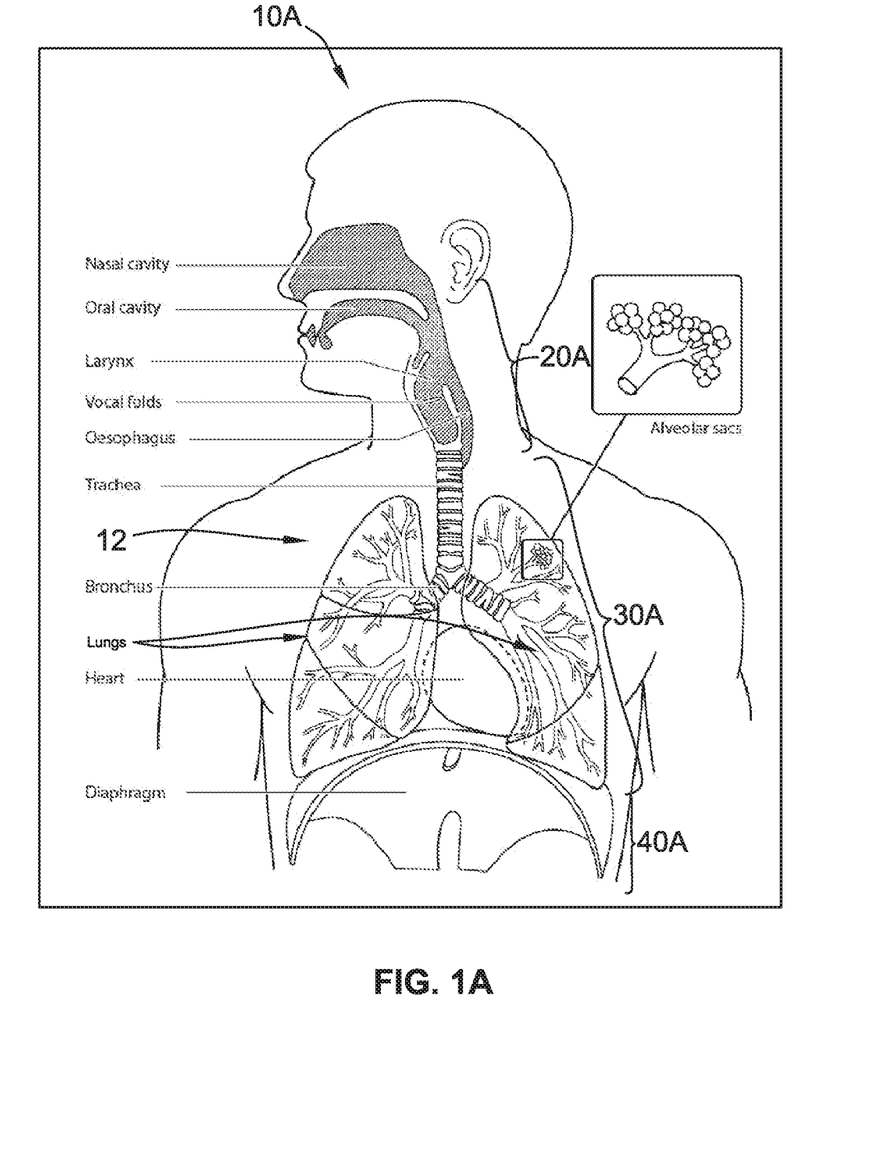
FIG. 1A is a diagram that illustrates an overview of a respiratory system of a user.

Referring to FIG. 1A, an overview of a respiratory system 12 of a user 10A (e.g., patient) is shown, which generally includes a nasal cavity, an oral cavity, a larynx, vocal folds, an oesophagus, a trachea, a bronchus, lungs, alveolar sacs, a heart, and a diaphragm. More generally, the user 10A has a throat 20A, which includes a region(s) of the respiratory system 12 of the user 10A generally in the neck area of the user 10A. The diaphragm of the user 10A is a sheet of muscle that extends across the bottom of the rib cage of the user 10A. The diaphragm generally separates the thoracic cavity 30A of the user 10A, which contains the heart, lungs, and ribs, from the abdominal cavity 40A of the user 10A. As the diaphragm contracts, the volume of the thoracic cavity 30A increases and air is drawn into the lungs.

As is described below in greater detail, one or more stimulators of the present disclosure can be positioned on the user 10A (e.g., via one or more bands/collars/belts, etc.) to aid the user 10A, for example, in breathing while sleeping. For example, one or more stimulators can be positioned on or near the throat 20A of the user 10A (e.g., adjacent to one or more nerves innervating the muscles of the neck/throat and/or the diaphragm, and/or adjacent to one or more muscles in the neck/throat 20A of the user 10), on or near the thoracic cavity 30A and/or the abdominal cavity 40A (e.g., adjacent to the diaphragm of the user 10), or any combination thereof.

Figure 1B:
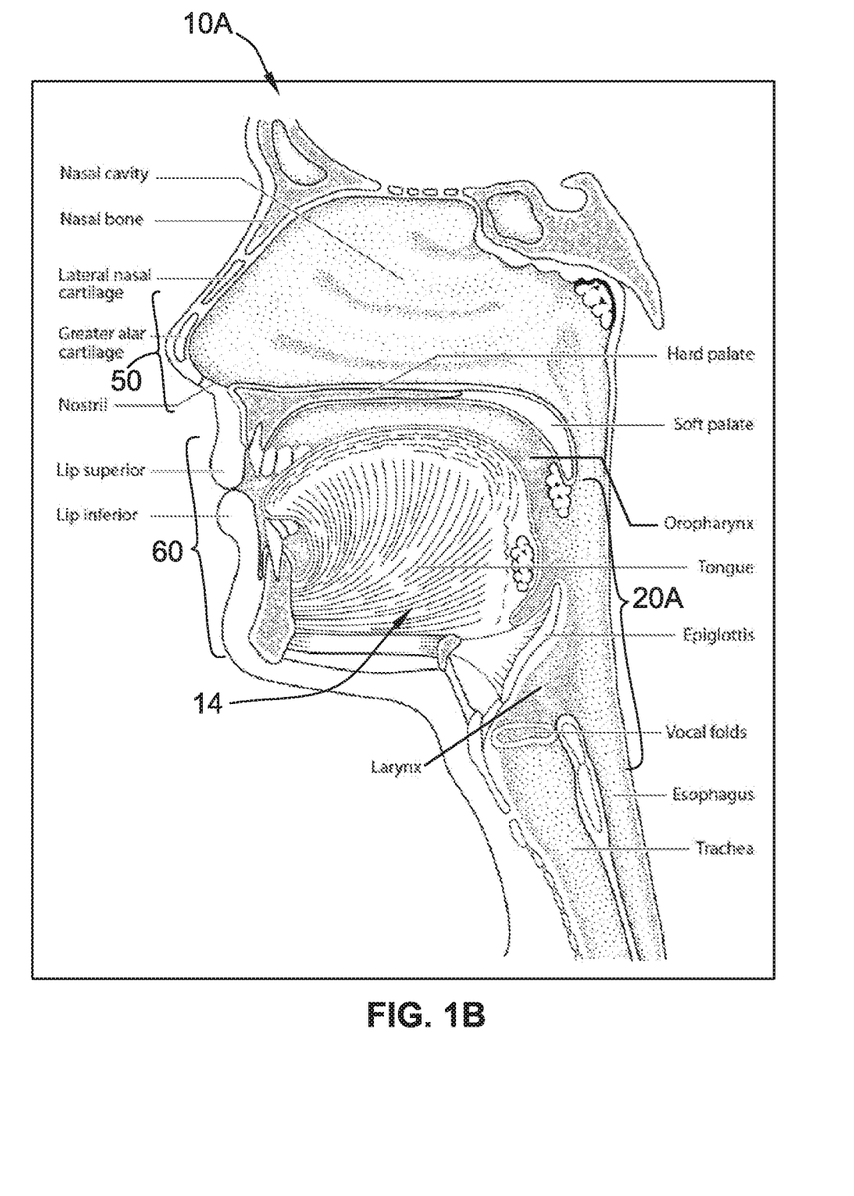
FIG. 1B is a diagram that illustrates an upper airway of the user of FIG. 1A.

Referring to FIG. 1B, a view of an upper airway 14 of the user 10A is shown, which includes the nasal cavity, nasal bone, lateral nasal cartilage, greater alar cartilage, nostrils (one shown), a lip superior, a lip inferior, the larynx, a hard palate, a soft palate, an oropharynx, a tongue, an epiglottis, the vocal folds, the oesophagus, and the trachea.

The respiratory system 12 of the user 10A facilitates gas exchange. The nose 50 and mouth 60 of the user 10 form the entrance to the airways of the user 10A. As best shown in FIG. 1A, the airways include a series of branching tubes, which become narrower, shorter, and more numerous as they penetrate deeper into the lungs of the user 10A. The prime function of the lungs is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lungs is where the gas exchange takes place, and is referred to as the respiratory zone.

A range of respiratory disorders exist that can impact the user 10A. Certain disorders are characterized by particular events (e.g., apneas, hypopneas, hyperpneas, or any combination thereof). Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and Chest wall disorders.

Obstructive Sleep Apnea (OSA) is a form of Sleep Disordered Breathing (SDB) and is characterized by events including occlusion and/or obstruction of the upper air passage during sleep. OSA results from a combination of an abnormally small upper airway and the normal loss of muscle tone in the region of the tongue, soft palate, and posterior oropharyngeal wall during sleep. The condition causes the affected patient to stop breathing for periods typically of 30 to 120 seconds in duration, sometimes 200 to 300 times per night. OSA often causes excessive daytime somnolence, and it may cause cardiovascular disease and brain damage. The syndrome is a common disorder, particularly in middle aged overweight males, although a person affected may have no awareness of the problem.

Cheyne-Stokes Respiration (CSR) is another form of sleep disordered breathing. CSR is a disorder of a user's respiratory controller in which there are rhythmic alternating periods of waxing and waning ventilation known as CSR cycles. CSR is characterized by repetitive de-oxygenation and re-oxygenation of the arterial blood. It is possible that CSR is harmful because of the repetitive hypoxia. In some users, CSR is associated with repetitive arousal from sleep, which causes severe sleep disruption, increased sympathetic activity, and increased afterload.

Respiratory failure is an umbrella term for respiratory disorders in which the lungs are unable to inspire sufficient oxygen or exhale sufficient $CO_2$ to meet the user's needs. Respiratory failure may encompass some or all of the following disorders.

A user with respiratory insufficiency (a form of respiratory failure) may experience abnormal shortness of breath on exercise.

Obesity Hyperventilation Syndrome (OHS) is the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some users suffering from NMD are characterized by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) rapidly progressive disorders: characterized by muscle impairment that worsens over months and results in death within a few years (e.g. amyotrophic lateral sclerosis (ALS) and duchenne muscular dystrophy (DMD) in teenagers); (ii) variable or slowly progressive disorders: characterized by muscle impairment that worsens over years and only mildly reduces life expectancy (e.g. limb girdle, Facioscapulohumeral and myotonic muscular dystrophy). Symptoms of respiratory failure in NMD include: increasing generalized weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterized by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

According to some implementations of the present disclosure, a system (e.g., system 100, 200, 300) is provided to aid users (e.g., patients) experiencing respiratory events (e.g., apnea events) during sleep. An apnea typically occurs when air flow for a user falls below a predetermined threshold for a duration (e.g. 10 seconds). A first type of apnea event is called an obstructive apnea. Obstructive apneas typically occur when, despite user effort to breathe, some obstruction of the airway does not allow air to flow. A second type of apnea event is called a central apnea. Central apneas typically occur when an apnea is detected that is due to a reduction in breathing effort, or the absence of breathing effort, despite the airway being patent (e.g., open). A third type of apnea event is called a mixed apnea. Mixed apneas typically occur when a reduction or absence of breathing effort coincides with an obstructed airway.

Figure 2:
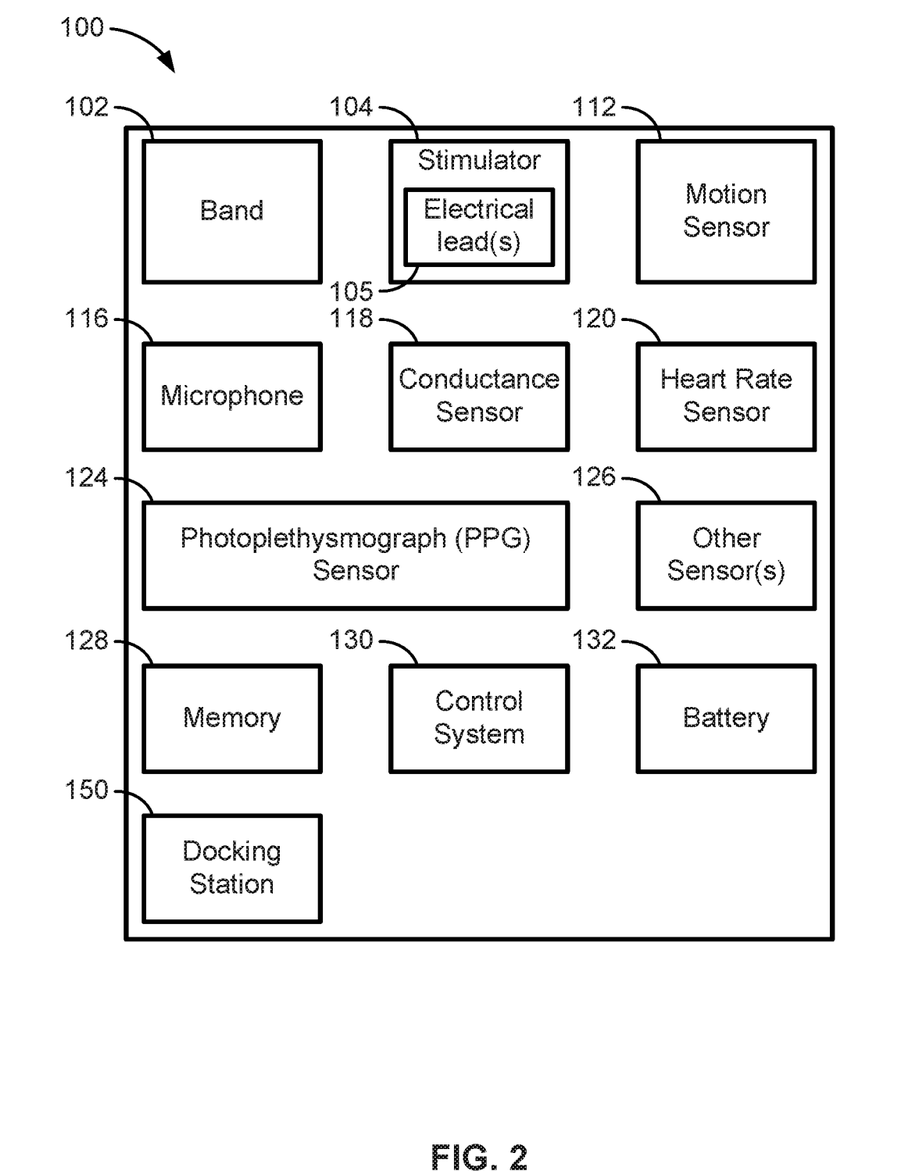
FIG. 2 is a block diagram of a system for aiding a user (e.g., in breathing during sleep), according to some implementations of the present disclosure.

Referring to FIG. 2, a block diagram of a system 100 for aiding a user (e.g., user 10A) is shown. The system 100 can aid the user 10A (i) in breathing while sleeping, (ii) in breathing while awake, (iii) in opening an airway of the user, (iv) in starting or increasing a breathing function (e.g., contracting a diaphragm), (v) or any combination thereof. In some implementations, the system 100 aids the user 10A by causing one or more muscles of the user 10A to contract to (i) open an airway of the user 10A, (ii) to cause the user 10A to inhale air (e.g., breathing effort), or (iii) both.

The system 100 includes one or more of: a band 102 (e.g., a collar, a chest band, a torso band, a waist band, a belt, etc., or the like), a stimulator 104, a motion sensor 112, a microphone 116, a conductance sensor 118, a heart rate sensor 120, a photoplethysmography (PPG) sensor 124, one or more other sensors 126 (e.g., EKG sensor, EEG sensor, EMG sensor, blood flow sensor, respiration sensor, pulse sensor, etc.), a memory 128, a control system 130, a battery 132, a docking station 150, or any combination(s) thereof. That is the system 100 can include any portion of and any combination of these elements and the elements can be combined in various different arrangements (e.g., physical and/or wireless) and/or housings.

According to some implementations of the present disclosure, a portion of the elements of the system 100 are coupled to and/or built into the band 102 such that the system 100 (e.g., or a portion of the system 100) is worn/donned by the user 10A during use of the system 100 by positioning the band 102 around a portion of the body of the user 10A (e.g., the neck of the user 10A, the chest of the user 10A, the abdomen of the user 10A, the torso of the user 10A, etc.). In some implementations, all of the elements of the system 100, except for the docking station 150, are coupled to or built into the band 102 and worn by the user 10A during use of the system 100.

The stimulator 104 is coupled to and/or built into the band 102. As such, when the band 102 is worn around a neck of the user 10A, one or more electrical leads 105 of the stimulator 104 are positioned adjacent to one or more muscles of the user 10A and/or one or more nerves of the user 10A that are connected to the one or more muscles of the user 10.

In some implementations, the one or more electrical leads 105 includes a first electrical lead 105 that is positioned to stimulate a first one of the one or more muscles and/or a first one of the one or more nerves. Similarly, a second electrical lead 105 is positioned to stimulate a second one of the one or more muscles and/or a second one of the one or more nerves. In some such implementations, the first electrical lead 105 is positioned on a first side of the airway of the user 10A and the second electrical lead 105 is positioned on a second opposing side of the airway of the user 10A.

In some implementations, the first electrical lead 105 provides the electrical stimulation at a first frequency and the second electrical lead 105 provides the electrical stimulation at a second frequency that is different from the first frequency. In some implementations, the first electrical lead 105 provides the electrical stimulation at a first intensity and the second electrical lead 105 provides the electrical stimulation at a second intensity that is different from the first intensity.

In some alternative implementations, the stimulator 104 is leadless. In such alternative implementations, the stimulator 104 is coupled to and/or built into the band 102 such that one or more ends of a body of the stimulator 104 protrude from the band 102 to contact skin of the user 10A and act as electrodes.

Once the band 102 is worn around the neck of the user 10A, the stimulator 104 is capable of delivering electrical and/or magnetic stimulation to the user 10A to aid in causing the one or more muscles of the user 10A to contract. The contraction of the one or more muscles of the user 10A can aid in opening an airway of the user 10A. The contraction can alternatively or additionally aid in causing the user 10A to have breathing effort (e.g., causing the diaphragm to draw/suck in air).

The electrical stimulation can be applied directly (e.g., through the skin of the user 10A) to the one or more muscles of the user 10A (e.g., muscles in the throat 20A of the user 10A, muscles surrounding and/or adjacent to an airway of the user 10A, the diaphragm of the user 10A, etc., or any combination thereof) and/or directly (e.g., through the skin of the user 10A) to the one or more nerves that are connected to the one or more muscles. Directing the electrical stimulation to the one or more nerves (as opposed to the one or more muscles directly) can allow for a relatively lower intensity (e.g., voltage, amperage, etc. or any combination thereof) of the electrical stimulation to be applied to cause the one or more muscles (connected to the one or more nerves) to contract.

The stimulator 104 includes or is an electrical conductor (e.g., one or more electrically conductive wires with or without a portion being electrically insulated). The stimulator 104 includes the one or more electrical leads 105, which are capable of carrying and/or flowing and delivering electrical current to the one or more muscles and/or one or more nerves of the user 10A. The electrical current can be supplied by the battery 132 or other power source that is directly and physically connected to the stimulator 104. The battery 132 can be rechargeable. In some implementations, the battery 132 can be recharged by the docking station 150 (e.g., when the system 100 is not being worn/used by the user 10A) in a wired or wireless fashion. Alternatively or in addition to the stimulator 104 including the battery 132, in some implementations, the electrical current is supplied by a wired connection (e.g., a wire connecting the system 100 to a wall outlet or the like).

In some implementations, the stimulator 104 only includes one or more electrically conductive wires, with or without a portion being electrically insulated. In some such implementations, the stimulator 104 has a length between about 1 millimeter and about 100 centimeters; between about 1 millimeter and about 100 millimeters; between about 1 millimeter and about 10 millimeters; or any length therebetween. Further, in some such implementations, the stimulator 104 has a diameter between about 0.01 millimeters and about 5 millimeters; between about 0.1 millimeter and about 2 millimeters; between about 0.1 millimeter and about 1 millimeter; or any diameter therebetween. The size and shape of the stimulator 104 can be selected such that the stimulator 104 can be built into the band 102.

In addition to the stimulator 104 being coupled to and/or built into the band 102, a number of other elements of the system 100 can be coupled to and/or built into the band 102 and worn around the neck of the user 10A. For example, in some implementations, the motion sensor 112, the microphone 116, the conductance sensor 118, the heart rate sensor 120, the photoplethysmography (PPG) sensor 124, the other sensor(s) 126, the memory 128, the control system 130, the battery 132, or any combination thereof can be coupled to and/or built into the band 102 along with the stimulator 104. By coupled to and/or built into the band 102 it is meant that the element(s) is completely incased within the band 102, attached to an exterior surface of the band 102, partially protruding from one or more openings in the band 102, directly or indirectly attached to the band 102, or any combination thereof.

One or more of various sensors can be included in the system 100. The sensors can generate data that can be analyzed by the control system 130 and/or by one or more other systems (e.g., mobile phones, computers, servers, cloud based devices, etc.). The analysis of the data is for determining information and/or to make decisions regarding the application and/or cessation of electrical stimulation to be applied to the user 10A via the stimulator 104.

In some such implementations, the system 100 includes the motion sensor 112. The motion sensor 112 can include one or more accelerometers, one or more gyroscopes, or any combination thereof. The motion sensor 112 can be used to generate motion data that is indicative of breathing or a lack thereof by the user 10A. In some implementations, the motion sensor 112 is coupled to and/or built into the band 102 such that, when the band 100 is worn around the neck/throat 20A (FIGS. 1A and 1B) of the user 10A, the motion sensor 112 is positioned adjacent to the airway of the user 10A. As such, the motion sensor 112 is able to generate data associated with movements or lack of movements of the airway that indicate breathing or a lack thereof (e.g., moving, expanding, retracting, etc. of the neck/throat 20A adjacent to an airway indicates breathing).

Similarly, in some other implementations, the motion sensor 112 is coupled to and/or built into the band 102 such that, when the band 100 is worn around the torso of the user 10A (e.g., around the thoracic cavity 30A and/or the abdominal cavity 40A), the motion sensor 112 is positioned adjacent to the lungs and/or diaphragm of the user 10A. As such, the motion sensor 112 is able to generate data associated with movements or lack of movements of the lungs and/or diaphragm that indicate breathing effort or a lack thereof (e.g., moving, expanding, retracting, etc. of the torso of the user 10A indicates breathing).

In addition to, or in lieu of, the motion sensor 112, the system 100 can include the microphone 116, the conductance sensor 118, the heart rate sensor 120, the PPG sensor 124, the other sensor(s) 126, or any combination thereof, where such sensors or portion thereof is coupled to and/or built into the band 102 in the same, or similar, fashion as described above for the motion sensor 112.

For example, in some implementations, the system 100 includes the PPG sensor 124 coupled to and/or built into the band 102. As such, the PPG sensor 124 is positioned adjacent to the throat 20A, or on the neck of the user 10A, when the band 102 is worn/donned by the user 10A (e.g., as a collar). In such implementations, the PPG sensor 124 is able to generate data that is indicative of blood flow of the user 10A adjacent to the airway, blood oxygen levels of the user 10A adjacent to the airway, heart rate of the user 10A, an apnea event the user 10A is currently experiencing, an apnea event the user 10A is likely to experience in the future, or any combination thereof.

For another example, in some implementations, the system 100 includes the microphone 116 coupled to and/or built into the band 102. As such, the microphone 116 is positioned adjacent to the throat 20A or torso of the user 10A when the band 102 is worn by the user 10A (e.g., as a collar, as a chest band, as a waist band, etc.). In such implementations, the microphone 116 is able to generate data (e.g., sound data) that is indicative of snoring, choking, an apnea event the user 10A is currently experiencing, an apnea event the user 10A is likely to experience in the future, or any combination thereof.

For another example, in some implementations, the system 100 includes the heart rate sensor 120 coupled to and/or built into the band 102. As such, the heart rate sensor 120 is positioned adjacent to the throat 20A or torso of the user 10A when the band 102 is worn by the user 10A (e.g., as a collar, as a chest band, as a waist band, etc.). In such implementations, the heart rate sensor 120 is able to generate data that is indicative a heart rate and/or pulse of the user 10A.

The other sensor(s) 126 that can be included in the system 100 and coupled to and/or built into the band 102 include, for example, a blood oxygen sensor, a blood flow sensor, a pulse sensor, a respiration sensor, an EKG sensor, an EMG sensor, a strain gauge, an accelerometer, or any combination thereof. Each of such other sensor(s) 126 can generate data that can be analyzed by the control system 130 and/or by one or more other systems to determine information and/or to make decisions regarding the application and/or cessation of electrical stimulation to be applied to the user 10A via the stimulator 104.

The memory 128 can include one or more physically separate memory devices, such that one or more memory devices can be coupled to and/or built into the band 102 and/or one or more external devices (e.g., mobile phones, computers, servers, cloud based devices, etc.) wirelessly coupled to the system 100. The memory 128 acts as a non-transitory computer readable storage medium on which is stored machine-readable instructions that can be executed by the control system 130 and/or one or more other systems. The memory 128 is also able to store (temporarily and/or permanently) the data generated by the sensors of the system 100. In some implementations, the memory 128 includes non-volatile memory, battery powered static RAM, volatile RAM, EEPROM memory, NAND flash memory, or any combination thereof. In some implementations, the memory 128 is a removable form of memory 128 (e.g., a memory card).

Like the memory 128, the control system 130 can be coupled to the band 102 and/or one or more external devices. The control system 130 is coupled to the memory 128 such that the control system 130 is configured to execute the machine-readable instructions stored in the memory 128. The control system 130 can include one or more processors and/or one or more controllers. In some implementations, the one or more processors includes one or more x86 INTEL processors, one or more processors based on ARM® Cortex®-M processor from ARM Holdings such as an STM32 series microcontroller from ST MICROELECTRONIC, or any combination thereof. In some implementations, the one or more processors include a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS.

In some implementations, the control system 130 is a dedicated electronic circuit. In some implementations, the control system 130 is an application-specific integrated circuit. In some implementations, the control system 130 includes discrete electronic components.

The control system 130 is able to receive input(s) (e.g., signals, generated data, instructions, etc.) from any of the other elements of the system 100 (e.g., the sensors, etc.). The control system 130 is able to provide output signal(s) to cause one or more actions to occur in the system 100 (e.g., to cause the stimulator 104 to provide electrical stimulation to the user 10A, etc.).

The control system 130 is able to analyze the data generated by any of the sensors of the system 100 to determine (i) if the user 10A is experiencing an apnea event, (ii) if the user 10A is about to experience an apnea event, (iii) if the user 10A is no longer experiencing an apnea event, (iv) a current sleep state of the user 10A, (v) a tension of the one or more muscles of the user 10A, (vi) or any combination thereof. Based on one or more of such determinations, the control system 130 is able to cause the stimulator 104 to provide electrical and/or magnetic stimulation to the user 10A to (i) aid in stopping an apnea event currently being experienced by the user 10A and/or (ii) aid in preventing an apnea event about to be experienced by the user 10A. In some such implementations, the control system 130 transmits a signal (wired or wireless) to cause the electrical stimulation of the one or more muscles of the user 10A.

In addition to causing the stimulator 104 to provide the electrical and/or magnetic stimulation, the control system 130 is able to vary one or more parameters of the electrical stimulation provided by the stimulator 104. The one or more parameters of the stimulation include frequency, intensity, duration, dwell time, rise time in a pulse, a ratio of on-time to an off-time, or any combination thereof.

In some implementations, the one or more parameters of the stimulation are varied based on a measured response (e.g., using one or more of the sensors of the system 100) of the one or more muscles to the stimulation. In some implementations, the modification to the parameters can be based on a continuous feedback loop by the control system 130 continuing to analyze the data generated by one or more of the sensors of the system 100 (e.g., the motion sensor 112, the PPG sensor 124, etc., or any combination thereof). As such, the control system 130 is able to modify (e.g., in real-time, while the user 10A is experiencing the same apnea event, after the user 10A experiences an apnea event but before the user 10A experiences another apnea event, etc.) one or more of the parameters based on the continued analysis.

For example, if the continued analysis of the generated data from one or more of the sensors of the system 100 indicates that the user 10A is still experiencing an apnea event in the presence of the stimulation, the control system 130 can cause the stimulator 104 to increase the intensity of the stimulation applied to the user 10A. For another example, if the continued analysis indicates that the user 10A is no longer experiencing an apnea event after stimulation, the control system 130 can cause the stimulator 104 to stop providing the simulation to the user 10A. As such, the user 10A is less likely to be desensitized over time to the stimulation as compared to systems that continually apply stimulation (even when the user 10A is not experiencing an apnea event).

In some implementations, the control system 130 causes the stimulator 104 to automatically increase an intensity of the stimulation applied to the user 10A. As such, the intensity is likely to reach a level that causes the one or more muscles of the user 10A to contract without the intensity having to be set artificially high from the beginning of the stimulation.

As discussed above, the control system 130 can continually monitor the generated data to determine if a current level of the automatically increased intensity of the stimulation has caused the one or more muscles of the user 10A to contract. When the control system 130 determines that the current level has not caused the one or more muscles of the user 10A to contract, the control system 130 causes and/or permits the stimulator 104 to continue automatically increasing the intensity of the stimulation beyond the current level. Similarly, when the control system 130 determines that the current level has caused the one or more muscles of the user 10A to contract, the control system 130 causes the stimulator 104 to stop automatically increasing the intensity of the stimulation at the current level. As such, a proper intensity (e.g., not an artificially high intensity, which can be painful) for the stimulation for the user 10A is reached.

The band 102 can be in the form of a collar, a belt, a waist band, a chest band, a torso band, etc., or any combination thereof and that is worn/donned by the user 10A. In some such implementations, the band 102 is made entirely or at least partially from a stretchable material such that the band 102 can be at least partially held close to the skin of the user 10A when donned. For example, when the band 102 is worn around the neck/throat 20A of the user 10A as a collar, the band 102 can include stretchable material such that band/collar 102 is snug around the neck/throat 20A of the user 10A (without choking the user 10A). As such, when a PPG sensor 124 is included in the band/collar 102, the PPG sensor 124 can be held in close relationship to the neck/throat 20A of the user 10A, which can aid in providing more accurate data from the PPG sensor 124.

Additionally or alternatively to the band 102 form factor, the system 100 can be in the form of a patch that is able to be stuck to the skin of the user 10A (e.g., stuck to the neck/throat 20A of the user 10A). Other form factors for the system 100 are contemplated. For example, the system 100 can be in the form of a scarf, etc.

As discussed above, the control system 130 is able to determine if a user is experiencing or about to experience one or more types of apneas and to take one or more actions in response thereto. Additionally, the control system 130 is able to determine if a user is experiencing or about to experience one or more other respiratory events and/or respiration related diseases and to take one or more actions in response thereof. Such other respiratory events and/or respiration related diseases as discussed herein include, for example, hypopneas, hyperpneas, sleep disordered breathing, cheyne-stokes respiration, respiratory failure, obesity hyperventilation syndrome, chronic obstructive pulmonary disease, neuromuscular disease, chest wall disorders, or any combination thereof.

The control system 130 executes a respiration event determination algorithm for the determination of the presence of respiration events (e.g., apneas, hypopneas, hyperpneas, etc.). In some implementations, the respiration event determination algorithm receives as an input at least a portion of the data generated from one or more of the sensors of the system 100 and provides as an output a flag that indicates that a respiration event (e.g., an apnea, a hypopnea etc.) has been detected. In some implementations, the respiration event determination algorithm receives as an input at least a portion of the data generated from one or more of the sensors of the system 100 and provides as an output an instruction to activate the stimulator 104 to provide electrical stimulation to the user 10A. In some such implementations, the instruction includes instructions for setting at least a portion of the one or more parameters of the electrical stimulation to be provided by the stimulator 104.

In some implementations of the system 100, a respiration event or an apnea is detected when a function of respiratory flow rate falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In some implementations of the system 100, a respiration event or a hypopnea is detected when a function of respiratory flow rate falls below a second flow rate threshold for a predetermined period of time. The function may determine a peak flow rate, a relatively short-term mean flow rate, or a flow rate intermediate of relatively short-term mean and peak flow rate, for example an RMS flow rate. The second flow rate threshold is greater than the flow rate threshold used to detect apneas.

In some implementations of the system 100, a respiration event or an apnea is detected when a function of blood flow rate (e.g., determined at least partially using the PPG sensor 124) falls below a flow rate threshold for a predetermined period of time. The function may determine a peak flow rate, a relatively short-term mean flow rate, or a flow rate intermediate of relatively short-term mean and peak flow rate. The flow rate threshold may be a relatively long-term measure of flow rate.

The control system 130 executes a snore event determination algorithm for the determination of the presence of snoring related events (e.g., snoring, choking, etc.). In some implementations, the snoring event determination algorithm receives as an input at least a portion of the data generated from one or more of the sensors (e.g., the microphone 116, the motion sensor 112, etc.) of the system 100 and provides as an output (i) a flag that indicates that a snoring event (e.g., an apnea, a hypopnea etc.) has been detected, (ii) a metric of the extent to which snoring is present, or (iii) both (i) and (ii).

In some implementations of the system 100, the snore event determination algorithm may determine an intensity of a flow rate signal in the range of 30-300 Hz. Further, the snore event determination algorithm may filter the respiratory flow rate signal to reduce background noise.

The control system 130 executes an airway patency algorithm for the determination of the patency (e.g., openness) of a user's airway. In some implementations, the airway patency algorithm receives as an input a respiratory flow rate signal and determines the power of the signal in the frequency range of about 0.75 Hz and about 3 Hz. The presence of a peak in this frequency range is indicative of an open airway. The absence of a peak in this frequency range is indicative of a closed airway. In some implementations, the airway patency algorithm receives as an input a respiratory flow rate signal and determines the presence or absence of a cardiogenic signal. The absence of a cardiogenic signal is indicative of a closed airway.

The control system 130 executes a therapy parameter algorithm for the determination of one or more of the parameters (e.g., intensity, frequency, duration, etc.) of the stimulator 104. In some such implementations, the therapy parameter algorithm receives as an input the output(s) of one or more other algorithms described herein and outputs one or more values for the one or more parameters (e.g., intensity, frequency, duration, etc.) of the electrical stimulation provided by the stimulator 104.

While the system 100 is shown as including one band 102, one stimulator 104, and one battery 132, it is contemplated that the system 100 can include any number of bands 102 (e.g., one, two, three, five, etc.), the system 100 can include any number of stimulators 104 (e.g., one, two, three, five, ten, fifty, etc.), and the system 100 can include any number of batteries 132 (e.g., one, two, three, five, ten, etc.). The ratio of stimulators 104 to bands 102 can be one-to-one or a different ratio. For example, in some implementations, two or more stimulators 104 can be coupled to and/or built into one band 102.

According to some implementations, the system 100 includes the band 102, where the stimulator 104, the PPG sensor 124, the memory 128, the control system 130, and the battery 132 are all coupled to the band 102. According to some implementations, the system 100 includes the band 102, where the stimulator 104, the motion sensor 112, the memory 128, the control system 130, and the battery 132 are all coupled to the band 102.

According to some implementations, the system 100 includes the band 102, where the stimulator 104, the PPG sensor 124, and the battery 132 are all coupled to the band 102, and the memory 128 and the control system 130 are separate and distinct from the band 102 (e.g., included in a remote device such as, for example, a mobile phone, a computer, a server, a cloud computer, etc.). In such implementations, the system includes wireless communication modules to permit the transmission and receiving of data and/or instructions between the control system 130 and the components coupled to the band 102.

A method of using the system 100 to aid the user 10A when experiencing an apnea event is now described. The control system 130 executes a respiration event determination algorithm for the determination of the presence of respiration events in the user 10A. In some such implementations, the respiration event determination algorithm is stored as instructions in the memory 128.

The control system 130 analyzes data generated by one or more of the sensors (e.g., the motion sensor 112, the PPG sensor 124, etc.) of the system 100 coupled to and/or built into the band 102 to determine if the user 10A is currently experiencing an apnea event (e.g., an obstructive apnea event). If the control system 130 determines that the user 10A is currently experiencing an apnea event, the control system 130 causes the stimulator 104 to provide stimulation. The stimulation can be provided to one or more muscles and/or one or more nerves of the user 10A that are adjacent to the throat 20A, chest 30A, and/or abdomen 40A of the user 10. The stimulation can aid in stopping the apnea event (e.g., by causing the one or more muscles in the throat 20A to contract and open the airway of the user 10A, by causing the diaphragm to contract and cause breathing function in the user 10A, or both).

Figure 3A:
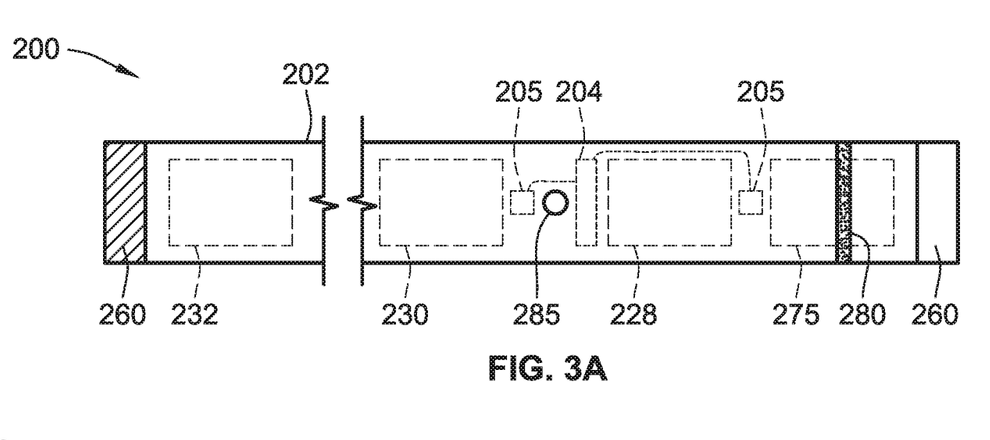
FIG. 3A is a front plan view of a system (unrolled) in the form of a band/collar for aiding a user (e.g., in breathing during sleep), according to some implementations of the present disclosure.
Figure 3B:
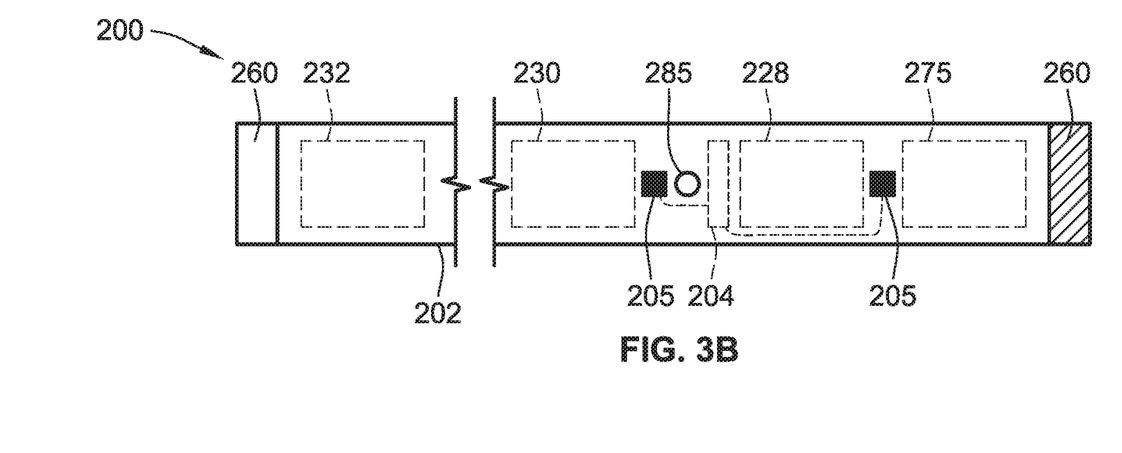
FIG. 3B is a rear plan view of the system (unrolled) of FIG. 3A.

Referring to FIGS. 3A and 3B, a system 200 includes a band 202 in the form of a collar. The band 202 is illustrated in an unrolled form to better illustrate the various aspects of the system 200. The system 200 is shown relative to a user 10B in FIG. 3C, where the band 202 is worn as a collar around a neck/throat 20B of the user 10B. The system 200 is the same as, or similar to, the system 100. The system 200 generally includes the band 202, a stimulator 204, a sensor 275, a memory 228, a control system 230, and a battery 232.

As shown in FIG. 3A, the stimulator 204, the sensor 275, a memory 228, a control system 230, and a battery 232, are all coupled to and/or built into the band 202. In some such implementations, the sensor 275 is built into the band 202 such that all of or a portion of the sensor 275 is obscured (e.g., hidden) by the band 202. Similarly, the memory 228, the control system 230, and the battery 232 are built into the band 202 such that all of or a portion of the memory 228, the control system 230, and the battery 232 is obscured (e.g., hidden) by the band 202.

The sensor 275 is the same as, or similar to, the motion sensor 112, the microphone 116, the conductance sensor 118, the heart rate sensor 120, the PPG sensor 124, the other sensor(s) 126, or any combination thereof. The memory 228 is the same as, or similar to, the memory 128 described herein in connection with FIG. 2. The control system 230 is the same as, or similar to, the control system 130 described herein in connection with FIG. 2. The battery 232 is the same as, or similar to, the battery 132 described herein in connection with FIG. 2.

Figure 3C:
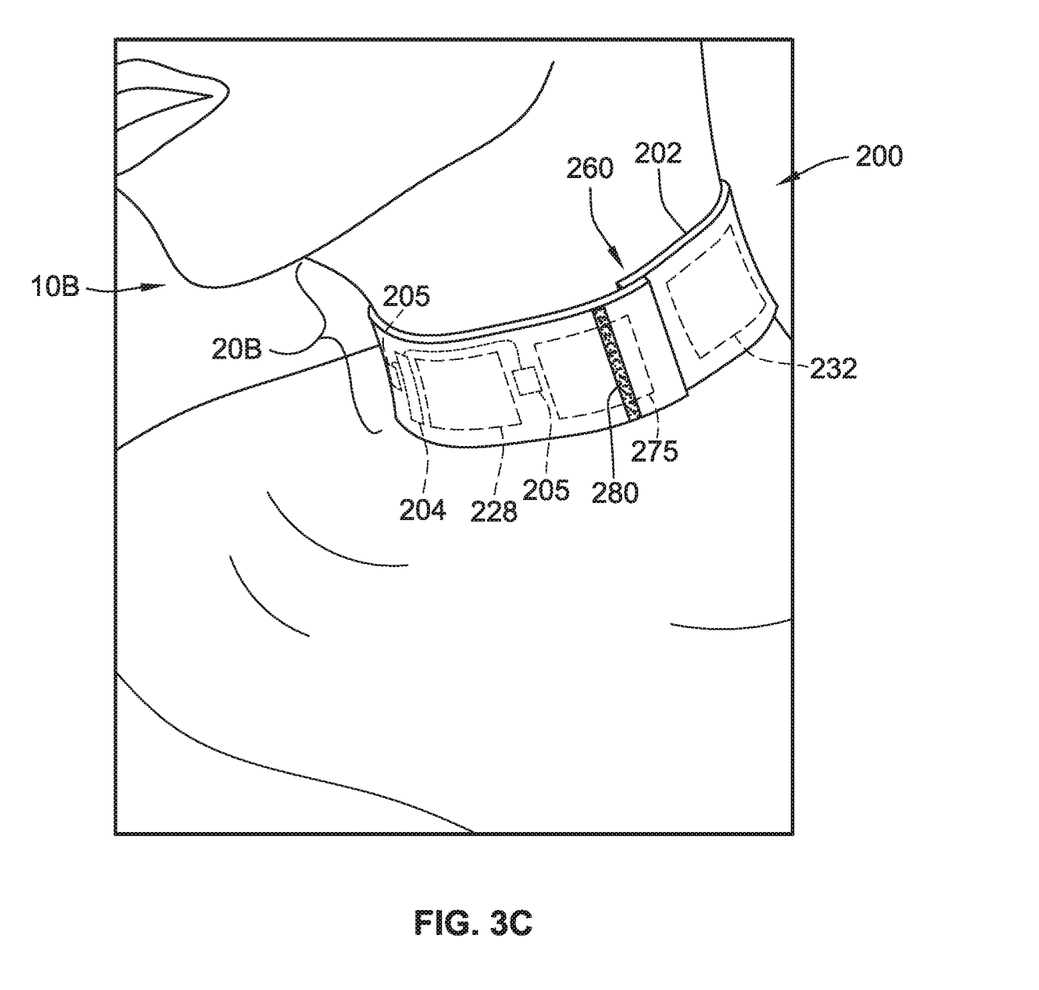
FIG. 3C is a perspective view of the system of FIG. 3A worn/donned by the user.

The stimulator 204 is the same as, or similar to, the stimulator 104 described herein in connection with FIG. 2. The stimulator 204 is shown with two electrical leads 205 that are exposed on a rear of the band 202 as shown in FIG. 3B. As such, the electrical leads 205 are able to directly engage (e.g., touch, contact, abut, etc., or any combination thereof) skin of the user 10B adjacent to one or more muscles of the user 10B when the band 202 is worn by the user 10B (FIG. 3C). While the system 200 is shown as including two electrical leads 205, the system 200 can include any number of electrical leads 205 (e.g., one electrical lead, three electrical leads, five electrical leads, ten electrical leads, etc.).

In some alternative implementations, the stimulator 204 is leadless (not shown). In such alternative implementations, the stimulator 204 is coupled to and/or built into the band 202 such that one or more ends of a body of the stimulator 204 protrude from the band 202 to contact skin of the user 10B and act as electrodes.

The stimulator 204 is coupled to and/or built into the band 202 such that when the band 202 is worn around the neck/throat 20B of the user 10B (FIG. 3C) and aligned, the stimulator 204 is positioned to provide electrical stimulation to one or more muscles in the throat 20B and/or the neck of the user 10B. As such, the stimulator 204 can aid in opening an airway of the user 10B. By aligned, it is meant that a circumferential position of the band 202 is in a predetermined position and/or range of positions about the neck 20B of the user 10B relative to one or more portions of the anatomy of the user 10B.

In some implementations, indicia can be included on the band 202 to aid the user 10B in aligning the band 202 with one or more portions of the anatomy of the user 10B. As such, the simulator 204, the electrical leads 205, the sensor 275, or any combination thereof are appropriately placed relative to the user 10B. For example, a vertical line indicium 280 can be included (e.g., printed) on an external surface of the band 202. The vertical line indicium 280 can indicate to the user 10B a location of the stimulator 204, one or more of the electrical leads 205, the sensor 275, or any combination thereof to be aligned with the user's anatomy (e.g., midline of the throat 20B, an ear of the user 10B, a rear edge of a jaw of the user 10B, a chin of the user 10B, etc.).

For another example, the band 202 can include other features to aid the user 10B in aligning the band 202 when donning the band 202. For example, a cutout 285 (e.g., having a circular shape, a square shape, a triangular shape, a polygonal shape, etc. or any combination thereof) in the band 202 can indicate a location of the band 202 that should be aligned with a specific part of the user's anatomy (e.g., midline of the throat 20B) such that, for example, the stimulator 204, one or more of the electrical leads 205, the sensor 275, or any combination thereof is appropriately placed relative to the user 10B. The cutouts are distinguishable by touch such that the user 10B can feel the cutouts when donning the band 202 and can use the cutouts to align the band 202 (e.g., without having to look in a mirror, in the dark, etc.). In some implementations, the band 202 includes a number of cutouts (e.g., a circular cutout to be aligned with a chin of the user 10B and two triangular cutouts to be aligned with ears of the user 10B).

By appropriately placed, it is meant, for example, that (i) the electrical lead(s) 205 are positioned in location(s) to apply electrical stimulation to the user 10B such that the one or more target muscles of the user 10B contract and aid in opening an airway of the user, (ii) the sensor 275 is positioned in a location relative to the user 10B such that the sensor 275 is able to generate reliable and/or usable data, or both. In some such implementations, the location of the sensor 275 depends on the type of sensor(s) included in the sensor 275. For example, if the sensor 275 is a motion sensor, the appropriate location for the sensor 275 maybe be in a first location and if the sensor 275 is a PPG sensor, the appropriate location for the sensor 275 maybe be in a second location that is the same or different from the first location.

As described herein, the band 202 is in the form of a collar that is wearable by the user 10B around the throat 20A/neck of the user 10B. The band 202 can be made of any type of material(s) (e.g., one or more types of plastic, one or more types of metal, nylon, one or more types of fabric, stretchable fabric, etc., or any combination thereof) suitable for being worn on a human body (e.g., neck).

The band 202 can include any type of coupling mechanism 260 (FIGS. 3A and 3B) to aid in attaching the band 202 about the neck and/or throat 20B of the user 10B. For example, the coupling mechanism 260 can include a hook and loop fastener, a magnetic clasp, a snap connection, a ball clasp, a bead clasp, a barrel clasp, a fishhook clasp, a push button clasp, a springing clasp, a lobster claw clasp, a hook and loop clasp, etc. or any combination thereof.

In some implementations, the coupling mechanism 260 includes a loop at one end of the band 202 into which the opposite end of the band 202 fits through and doubles back to secure to an outside surface of the band 202 using, for example, hook and loop fasteners. Various other ways of securing the band 202 about the user 10B are contemplated. In some implementations, the coupling mechanism 260 aids in securing the band 202 to the user 10B in a snug fashion. Alternatively, the coupling mechanism 260 aids in securing the band 202 to the user 10B in a loose fashion.

Figure 4:
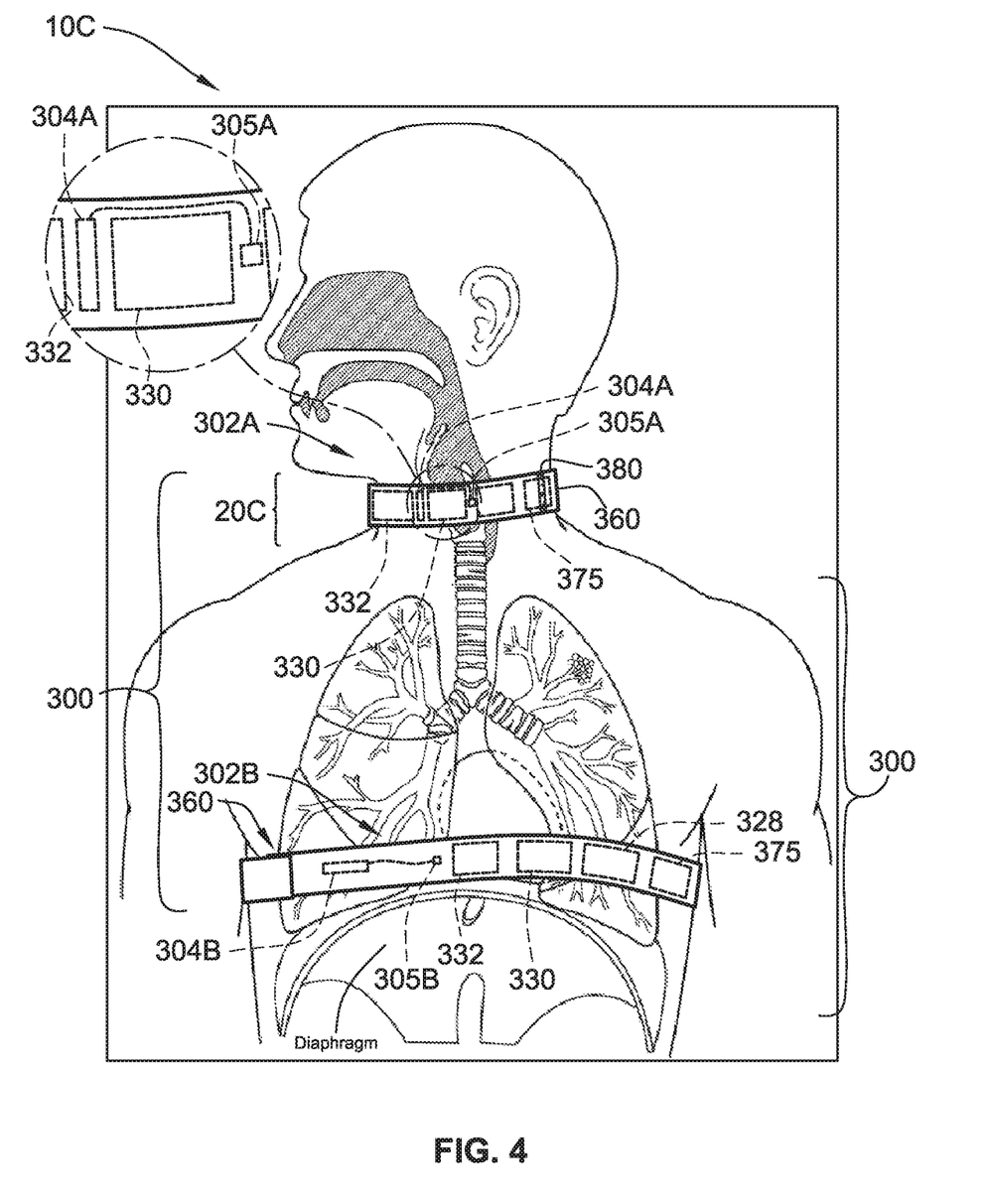
FIG. 4 is a cross-sectional diagram view of a user wearing a system including two bands for aiding the user (e.g., in breathing during sleep), according to some implementations of the present disclosure.

Referring to FIG. 4, a system 300 is shown relative to a cross-sectional diagram of a user 10C. The system 300 is the same as, or similar to, the systems 100, 200. The system 300 mainly differs in that the system 300 includes two stimulators and two bands that work together to aid the user 10C.

The system 300 includes a first band 302A that can be worn about a throat 20C of the user 10C and a second band 302B that can be worn generally about a torso 30C (e.g., chest, abdomen, waist, etc.) of the user 10C. The first band 302A can be referred to as a collar and the second band 302B can be referred to as a chest band. The first and second bands 302A, 302B are the same as, or similar to, the bands 102, 202 described herein in connection with FIGS. 2, 3A, 3B, and 3C.

The first band 302A is coupled to or includes built therein, the first stimulator 304A with one or more electrical leads 305A, a sensor 375, a memory 328, a control system 330, a battery 332, and a coupling mechanism 360, which are the same as, or similar to, the stimulator 104, 204, the sensor 275, the memory 128, 228, the control system 130, 230, the battery 132, 232, and the coupling mechanism 260 of the system 100, 200 described in connection with FIGS. 2A-3C. The first band 302A also includes a vertical line indicium 380 (e.g., printed thereon) on an external surface of the first band 302A, which is the same as, or similar to, the vertical line indicium 280.

Similarly, the second band 302B is coupled to or includes built therein, the second stimulator 304B with one or more electrical leads 305B, a sensor 375, a memory 328, a control system 330, a battery 332, and a coupling mechanism 360, which are the same as, or similar to, the stimulator 104, 204, the sensor 275, the memory 128, 228, the control system 130, 230, the battery 132, 232, and the coupling mechanism 260 of the system 100, 200 described in connection with FIGS. 3A-3C. The second band 302B mainly differs from the first band 302A in size. Namely, the second band 302B is larger (e.g., longer) such that the second band 302B can be worn around a torso 30C of the user 10C.

In some implementations, the first band 302A and the first stimulator 304A are able to operate independently from the second band 302B and the second stimulator 304B. In such implementations, the first band 302A (and its components coupled thereto) forms a first sub-system of the system 300 that aid the user 10C in addressing a first type of apnea events (e.g., obstructive apneas). For example, the first sub-system causes muscles in the throat 20C to contract to open an airway. Similarly, in such implementations, the second band 302B (and its components coupled thereto) forms a second sub-system of the system 300 that aid the user 10C in addressing a second type of apnea events (e.g., central apneas). For example, the second sub-system causes the diaphragm of the user 10C to contract to aid breathing effort of the user 10C. In such implementations, both the first band 302A (collar) and the second band 302B (torso band) include respective memories 328 and respective control systems 330. In some such implementations, the first and second sub-systems coordinate therapy such that the stimulation that is applied by the first and second sub-systems is coordinated (e.g., at the same time, alternating, etc.).

In some alternative implementations, the first and second bands 302A, 302B are not able to operate independently and are coupled together (e.g., wirelessly and/or wired). In such implementations, only one of the first and second bands 302A, 302B includes the memory 328 and the control system 330. That is, for example, the second band 302B (torso band) includes the memory 328 and the control system 330 and the first band 302A (collar) does not include a memory and nor a control system. For another example, the first band 302A (collar) includes the memory 328 and the control system 330 and the second external device 350B (torso band) does not include a memory nor a control system.

It should be understood that the sensor 375 coupled to the first band 302A and the sensor 375 coupled to the second band 302B can be the same type of sensor(s) or different sensor(s). For example, in some implementations, the sensor 375 coupled to the first band 302A (collar) is a PPG sensor (e.g., like the PPG sensor 124) and the sensor 375 coupled to the second band 302B (torso band) is a motion sensor (e.g., like the motion sensor 112). The sensor 375 of the first band 302A and/or the sensor 375 of the second band 302B can include any number of sensors (e.g., different types of sensors or more than one of the same type of sensors).

A method of using the system 300 to aid the user 10C when experiencing one or more types of apnea events is now described. The control system 330 (in the first band 302A, in the second band 302B, or a combination thereof) executes a respiration event determination algorithm for the determination of the presence of respiration events in the user 10C. In some such implementations, the respiration event determination algorithm is stored as instructions in the memory 328 (in the first band 302A, in the second band 302B, or a combination thereof).

The control system 330 analyzes data generated by the sensor 375 coupled to the first band 302A to determine if the user 10C is currently experiencing a first type of apnea event (e.g., an obstructive apnea event). The control system 330 also analyzes data generated by the sensor 375 coupled to the second band 302B to determine if the user 10C is currently experiencing a second type of apnea event (e.g., a central apnea event).

If the control system 330 determines that the user 10C is currently experiencing the first type of apnea event, the control system 330 causes the first stimulator 304A to provide electrical stimulation via the one or more electrical leads 305A. The electrical stimulation can be provided to one or more muscles and/or one or more nerves of the user 10C that are adjacent to the throat 20C of the user 10C. The electrical stimulation can aid in stopping the first type of apnea event (e.g., by causing the one or more muscles in the throat 20C to contract and open the airway of the user 10C).

If the control system 330 determines that the user 10C is currently experiencing the second type of apnea event, the control system 330 causes the second stimulator 304B to provide electrical stimulation via the one or more electrical leads 305B. The electrical stimulation can be provided to the diaphragm and/or one or more nerves connected to the diaphragm of the user 10C. The electrical stimulation can aid in stopping the second type of apnea event (e.g., by causing the diaphragm to contract and cause the user 10C to breathe/suck air into the respiration system).

Further, if the control system 330 determines that the user 10C is currently experiencing the first type of apnea event and the second type of apnea event at the same time, the control system 330 (i) causes the first stimulator 304A to provide electrical stimulation to the one or more muscles and/or one or more nerves of the user 10C that are adjacent to the throat 20C of the user 10C and (ii) causes the second stimulator 304B to provide electrical stimulation to the diaphragm and/or one or more nerves connected to the diaphragm of the user 10C.

In some implementations, the electrical leads 105, 205, 305A, 305B of the present disclosure are sized and shaped to protrude from the band 102, 202, 302A, 302B such that donning of the band 102, 202, 302A, 302B causes the electrical lead(s) to 105, 205, 305A, 305B press into the skin of the user 10A, 10B, 10C. In some such implementations, the leads 105, 205, 305A, 305B extend from the band 102, 202, 302A, 302B by a distance of about 0.1 inches, about 0.25 inches, about 0.5 inches, about 0.75 inches, about one inch, etc. or any distance in between.

One or more elements or aspects or steps, or any portion(s) thereof, from one or more of any of the claims below can be combined with one or more elements or aspects or steps, or any portion(s) thereof, from one or more of any of the other claims below or combinations thereof, to form one or more additional implementations and/or claims of the present disclosure.

While the present disclosure has been described with reference to one or more particular embodiments and implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

What is claimed is:

1. A method for aiding a user in breathing during sleep, the method comprising:
   receiving, from a first sensor, first data;
   receiving, from a second sensor, second data;
   analyzing the first data to determine if the user is currently experiencing a first type of apnea event;
   analyzing the second data to determine if the user is currently experiencing a second type of apnea event that is different than the first type of apnea event;
   in response to determining that the user is currently experiencing the first type of apnea event based on the analyzing the first data, causing a first stimulator to provide electrical stimulation to one or more muscles of the user that are adjacent to an airway of the user to aid in stopping the first type of apnea event, the first stimulator and the first sensor being coupled to a first band that is configured to be worn around a neck of the user; and
   in response to determining that the user is currently experiencing the second type of apnea event based on the analyzing the second data, causing a second stimulator to provide the electrical stimulation to a diaphragm of the user to aid in stopping the second type of apnea event, the second stimulator and the second sensor being coupled to a second band that is configured to be worn around a chest or an abdomen of the user.

2. The method of claim 1, wherein the first type of apnea event is an obstructive apnea event and the second type of apnea event is a central apnea event.

3. The method of claim 1, wherein the first sensor is a photoplethysmography (PPG) sensor, and wherein the first data includes data associated with blood flow of the user.

4. The method of claim 3, wherein the second sensor is a motion sensor, a strain gauge, an accelerometer, or any combination thereof, and wherein the second data includes data associated with movement of a chest of the user, one or more muscles of an abdomen of the user, or both.

5. The method of claim 1, wherein the first sensor is a first type of sensor and the second sensor is a second type of sensor that is different than the first type of sensor.

6. A system for aiding a user in breathing during sleep, the system comprising:
   a first band configured to be worn around a neck of the user;
   a first stimulator coupled to the first band such that, when the first band is worn around the neck of the user, the first stimulator is positioned to provide electrical stimulation to one or more muscles of the user that are adjacent to an airway of the user;
   a second band configured to be worn around a chest or abdomen of the user;
   a second stimulator coupled to the second band such that, when the second band is worn around the chest or abdomen of the user, the second stimulator is positioned to provide electrical stimulation to a diaphragm of the user;

a first sensor coupled to the first band and configured to generate first data;

a second sensor coupled to second band and configured to generate second data;

a memory storing machine-readable instructions; and a control system including one or more processors configured to execute the machine-readable instructions to:

analyze the generated first data to determine if the user is currently experiencing a first type of apnea event;

analyze the generated second data to determine if the user is currently experiencing a second type of apnea event that is different than the first type of apnea event;

in response to a determination that the user is currently experiencing the first type of apnea event, cause the first stimulator to provide the electrical stimulation to the one or more muscles of the user that are adjacent to the airway of the user to aid in stopping the first type of apnea event; and in response to a determination that the user is currently experiencing the second type of apnea event, cause the second stimulator to provide the electrical stimulation to the diaphragm of the user to aid in stopping the second type of apnea event.

7. The system of claim 6, wherein the first type of apnea event is an obstructive apnea event and the second type of apnea event is a central apnea event.

8. The system of claim 6, wherein the first sensor is a photoplethysmography (PPG) sensor, and wherein the first data includes data associated with blood flow of the user.

9. The system of claim 8, wherein the second sensor is a motion sensor, a strain gauge, an accelerometer, or any combination thereof, and wherein the second data includes data associated with movement of a chest of the user, one or more muscles of an abdomen of the user, or both.

10. The system of claim 6, wherein the first sensor is a first type of sensor and the second sensor is a second type of sensor that is different than the first type of sensor.

11. The system of claim 6, wherein the first band is adjustable such that a length of the first band can be altered when worn around the neck of the user.

12. The system of claim 11, wherein the second band is adjustable such that a length of the second band can be altered when worn around the chest or abdomen of the user.

13. The system of claim 12, wherein the first band, the second band, or both are at least partially stretchable.

14. The system of claim 6, wherein the memory and the control system are physically coupled to the second band and configured to wireless control the first stimulator.

15. The system of claim 6, wherein the memory and the control system are physically coupled to the first band and configured to wireless control the second stimulator.

16. The method of claim 1, further comprising analyzing the first data, the second data, or both to determine a sleep state of the user, a tension of the one or more muscles, or both.

17. The method of 1, further comprising varying one or more parameters of the electrical stimulation.

18. The method of claim 17, wherein the one or more parameters of the electrical stimulation are varied based at least in part on a measured response of the one or more muscles to the electrical stimulation.

19. The method of claim 18, wherein the one or more parameters of the electrical stimulation include frequency, intensity, duration, dwell time, rise time in a pulse, a ratio of on-time to an off-time, or any combination thereof.

20. The method of claim 1, wherein the one or more muscles of the user that are adjacent to the airway of the user include one or more muscles of a neck of the user, one or more muscles of a throat of the user, or both.

21. The system of claim 6, wherein the one or more muscles of the user that are adjacent to the airway of the user include one or more muscles of a neck of the user, one or more muscles of a throat of the user, or both.

22. The method of claim 3, wherein analyzing the first data to determine if the user is currently experiencing the first type of apnea event includes analyzing the first data to determine whether the blood flow rate of the user has fallen below a blood flow rate threshold.

23. The method of claim 22, wherein analyzing the first data to determine whether the blood flow rate of the user has fallen below the blood flow rate threshold includes analyzing the data to determine whether the blood flow rate of the user has fallen below the blood flow rate threshold for a predetermined period of time.

24. The system of claim 8, wherein analyzing the first data to determine if the user is currently experiencing the first type of apnea event includes analyzing the first data to determine whether the blood flow rate of the user has fallen below a blood flow rate threshold.

25. The system of claim 24, wherein analyzing the first data to determine whether the blood flow rate of the user has fallen below the blood flow rate threshold includes analyzing the data to determine whether the blood flow rate of the user has fallen below the blood flow rate threshold for a predetermined period of time.

26. The method of claim 1, wherein determining that the user is currently experiencing the first type of apnea event is based on only the first data, and wherein determining that the user is currently experiencing the second type of apnea event is based on only the second data.

27. The system of claim 6, wherein determining that the user is currently experiencing the first type of apnea event is based on only the first data, and wherein determining that the user is currently experiencing the second type of apnea event is based on only the second data.

* * * * *